United States Patent
Tian et al.

(10) Patent No.: US 10,494,377 B1
(45) Date of Patent: Dec. 3, 2019

(54) BERGENIN LIPOIC ACID ESTER WITH ANTIOXIDANT ACTIVITY AND A METHOD OF PREPARING THE SAME

(71) Applicants: Bin Tian, Xi'an (CN); Xingke Ju, Xi'an (CN); Lei Tian, Xi'an (CN); Jie Li, Xi'an (CN); Songsong Ruan, Xi'an (CN); Minyi Jia, Xi'an (CN); Danni Tian, Xi'an (CN); Han Li, Xi'an (CN); Qianqian Zhao, Xi'an (CN); Xuechuan Wang, Xi'an (CN); Chengyuan Liang, Xi'an (CN)

(72) Inventors: Bin Tian, Xi'an (CN); Xingke Ju, Xi'an (CN); Lei Tian, Xi'an (CN); Jie Li, Xi'an (CN); Songsong Ruan, Xi'an (CN); Minyi Jia, Xi'an (CN); Danni Tian, Xi'an (CN); Han Li, Xi'an (CN); Qianqian Zhao, Xi'an (CN); Xuechuan Wang, Xi'an (CN); Chengyuan Liang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/120,403

(22) Filed: Sep. 3, 2018

(51) Int. Cl.
*C07D 493/04* (2006.01)

(52) U.S. Cl.
CPC .................. *C07D 493/04* (2013.01)

(58) Field of Classification Search
CPC .................................................. C07D 493/039
USPC .......................................................... 549/39
See application file for complete search history.

(56) References Cited

PUBLICATIONS

Takashashi et al. Synthesis and neuroprotective activity of bernegin withantioxidant activity. (Year: 2003).*
Samanthi et al, Novel conjugates of 1,3-Diacylglycerol and Lipoic acid (Year: 2011).*
Koufaki et al, Multifunctional Lipoic Acid Conjugates. (Year: 2009).*

* cited by examiner

*Primary Examiner* — Rita J Desai

(57) ABSTRACT

A compound having the formula (I):

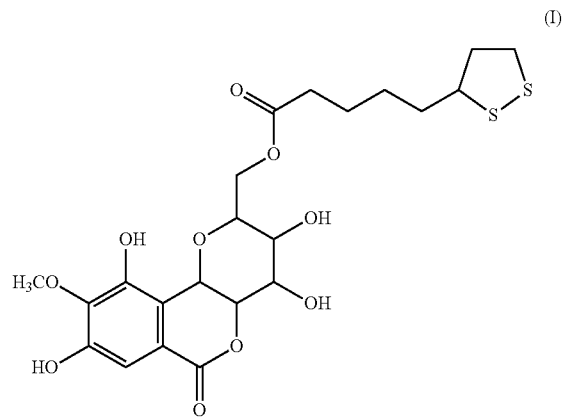

is disclosed. A method of preparing the compound of formula (I) is also disclosed.

6 Claims, 1 Drawing Sheet

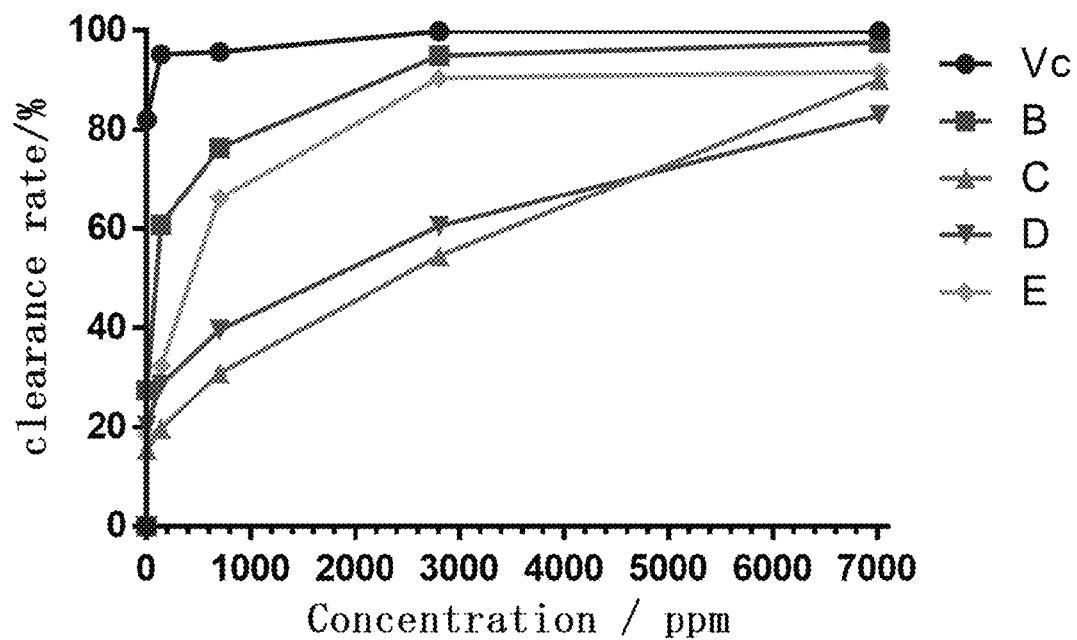

BERGENIN LIPOIC ACID ESTER WITH ANTIOXIDANT ACTIVITY AND A METHOD OF PREPARING THE SAME

The present invention claims priority to Chinese Patent Application No. CN 201810649372.5, filed on Jun. 22, 2018, which is incorporated by reference for all purposes as if fully set forth herein.

FIELD OF THE INVENTION

The present invention relates to food chemistry field, in particular, to a bergenin lipoic acid ester with antioxidant activity and a method of preparing the same.

BACKGROUND OF THE INVENTION

Bergenin (compound of formula II) is a dihydroisocoumarin derivative and is the main bioactive component of Saxifragaceae. In 1880, Garrean extracted the bergenin from the plant of the genus Huer, but did not complete its structural determination until 1958. Numerous studies have confirmed that bergenin has a variety of biological activities, including anti-cancer, anti-hepatotoxicity, anti-oxidation, anti-arrhythmia, anti-HIV and neuroprotective properties. In addition, studies have shown that bergenin has an antioxidative repair effect on tissue damage caused by 2,4-DNPH and alcoholism, and at the same time has a certain effect on eliminating the side effects of oxidants in blood and metabolism. Takahashi et al. (Takahashi H, Kosaka M, Watanabe Y, et al. Synthesis and neuroprotective activity of bergenin derivatives with antioxidant activity. Bioorganic & Medicinal Chemistry, 2003, 11(8): 1781-1788.) The bergenin was obtained from *Davidia involucrata*. It was found that bergenin has a good scavenging effect on DPPH free radicals and superoxide anions, and the antioxidant effect is remarkable. By modifying the sugar bond of bergenin by binding with various fatty acids, its antioxidant activity can be enhanced, indicating that the structural modification of bergenin provides the possibility of obtaining novel antioxidants.

Lipoic acid (LA) (compound of formula III), also known as α-lipoic acid (ALA), is a natural disulfide compound that was first isolated from pig liver by Reed in 1951. It is one of B vitamins. As a natural antioxidant, lipoic acid is a water-soluble and fat-soluble amphiphilic molecule. Both oxidized and reduced forms have strong antioxidant effects in both water and lipid environments. In addition, lipoic acid can exert anti-tumor effects by inhibiting tumor angiogenesis, enhancing immunity, increasing tumor sensitivity to chemotherapeutic drugs, and reversing tumor resistance, so lipoic acid has high medical value and anti-aging potential.

In the present invention, 11-hydroxyl group of bergenin is dehydrated and condensed with lipoic acid carboxyl group to form an ester bond, thereby obtaining a bergenin lipoic acid ester. Preliminary antioxidant experiments show that the compound has excellent antioxidant activity and has high medical research and application value in the field of antioxidant health products.

SUMMARY OF THE INVENTION

In one embodiment, the present invention provides a bergenin lipoic acid ester, which can be used as an excellent anti-oxidation and preparation of scavenging free radical products in the fields of food, health care products and medicine. The structural formula of the compound of the present invention is as shown in Formula (I):

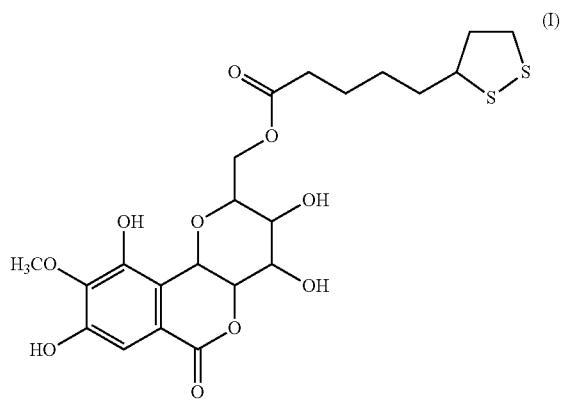 [SMILES: COc1c(O)cc2c(c1O)C1OC(COC(=O)CCCCC3CCSS3)C(O)C(O)C1OC2=O]

In another embodiment, present invention provides a method of preparing the compound of formula (I). The method includes reacting the compound of formula (II) with the compound of formula (III) to obtain the compound of formula (I):

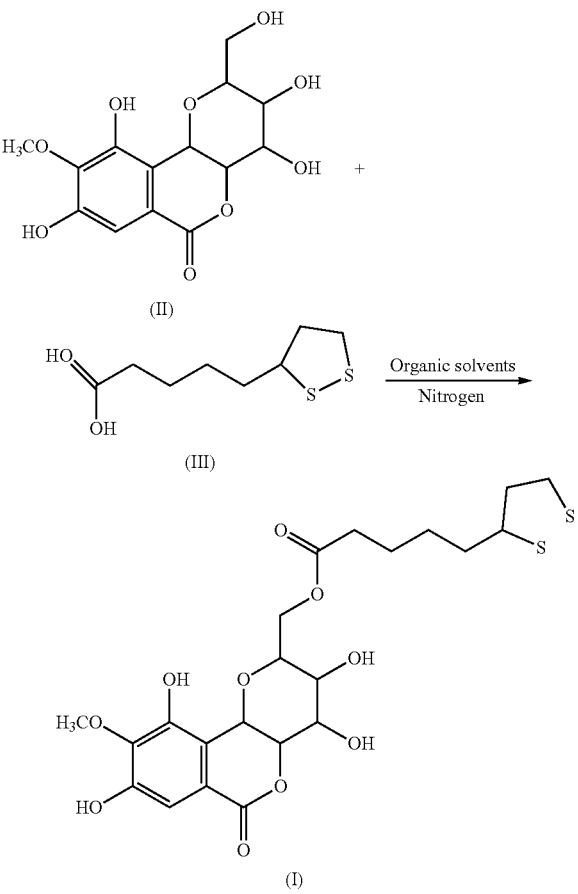

In another embodiment, the reaction of the compound of formula (II) with the compound of formula (III) includes the following steps: placing the compound of formula (II) and the compound of formula (III), in a molar ratio of 1:1 to 1:1.5, in a reactor under nitrogen atmosphere; adding an organic solvent and a catalyst to obtain a reaction mixture; and heating the reaction mixture at 50-60° C. for 10-12 hours under sonication.

In another embodiment, the organic solvent is acetonitrile or tetrahydrofuran.

In another embodiment, the organic solvent is acetonitrile.

In another embodiment, the molar ratio of the compound of formula (II) and the compound of formula (III) is 1:1.2.

In another embodiment, the catalyst is N,N'-dicyclohexylcarbodiimide (DCC), 1-ethyl-3-(3-dimethylaminopropyl)carbodiimide (EDC), or sulfuric acid.

In another embodiment, the catalyst 1-ethyl-3-(3-dimethylaminopropyl)carbodiimide.

In another embodiment, the reaction mixture is heated at 60° C.

In another embodiment, the reaction mixture is heated for 12 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the scavenging activity of the compound of formula (I) and control solutions at different concentrations.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of Bergenin Lipoic Acid Ester (Compound of Formula I)

In a 100 mL three-necked flask, 100 mg (0.31 mmoL) of bergenin and 77 mg (0.37 mmoL) of lipoic acid were dissolved in 40 mL of acetonitrile in a molar ratio of 1:1.2 under nitrogen atmosphere. A catalytic amount of EDC was slowly added under magnetic stirring, the temperature was raised to 60° C., and the reaction was carried out for 12 hours. The reaction was traced to completion by thin layer chromatography, and the heating was stopped. The reaction mixture system was transferred to a separatory funnel, and the lower phase was collected and concentrated to obtain crude bergenin lipoic acid ester. The crude bergenin lipoic acid ester was added to a pear-shaped separatory funnel, and water and chloroform were added. The lower organic layer was collected, dried over anhydrous sodium sulfate, and concentrated under reduced pressure to obtain bergenin lipoic acid ester, 88 mg, a yield of 54.2%.

$^1$H-NMR (300 MHz, DMSO-d$^6$) δ (ppm): 9.45-9.38 (2H, d), 6.87 (1H, s), 5.37 (1H, d), 5.05 (1H, m), 4.41-4.32 (3H, m), 4.12-4.05 (3H, m), 3.63-3.56 (4H, m), 2.51 (2H, m), 2.28-2.24 (3H, m), 1.67-1.50 (6H, m), 1.12 (2H, m); $^{13}$C-NMR (75 MHz, DMSO-d$^6$) δ (ppm): 167.7, 160.3, 143.1, 140.3, 139.0, 119.6, 111.5, 103.1, 75.5, 73.4, 70.0, 68.4, 55.3, 53.9, 50.3, 32.8, 28.7, 27.0, 23.6, 22.1; MS (ESI) for (M+H)+: 571.6.

Example 2

Preparation of Bergenin Lipoic Acid Ester

In a 100 mL three-necked flask, 150 mg (0.45 mmoL) of bergenin and 111 mg (0.54 mmoL) of lipoic acid were dissolved in 40 mL of acetonitrile in a molar ratio of 1:1.2 under nitrogen atmosphere. A catalytic amount of DCC was slowly added under magnetic stirring, the temperature was raised to 60° C., and the reaction was carried out for 12 hours. The reaction was traced to completion by thin layer chromatography, and the heating was stopped. The reaction mixture system was transferred to a separatory funnel, and the lower phase was collected and concentrated to obtain crude bergenin lipoic acid ester. The crude bergenin lipoic acid ester was added to a pear-shaped separatory funnel, and water and chloroform were added. The lower organic layer was collected, dried over anhydrous sodium sulfate, and concentrated under reduced pressure to obtain bergenin lipoic acid ester, 119 mg, a yield of 52.3%.

Example 3

Preparation of Bergenin Lipoic Acid Ester

In a 100 mL three-necked flask, 100 mg (0.31 mmoL) of bergenin and 77 mg (0.37 mmoL) of lipoic acid were dissolved in 40 mL of acetonitrile in a molar ratio of 1:1.2 under nitrogen atmosphere. A catalytic amount of concentrated sulfuric acid was slowly added under magnetic stirring, the temperature was raised to 60° C., and the reaction was carried out for 12 hours. The reaction was traced to completion by thin layer chromatography, and the heating was stopped. The reaction mixture system was transferred to a separatory funnel, and the lower phase was collected and concentrated to obtain crude bergenin lipoic acid ester. The crude bergenin lipoic acid ester was added to a pear-shaped separatory funnel, and water and chloroform were added. The lower organic layer was collected, dried over anhydrous sodium sulfate, and concentrated under reduced pressure to obtain bergenin lipoic acid ester, 77 mg, a yield of 48.4%.

Example 4

Preparation of Bergenin Lipoic Acid Ester

In a 100 mL three-necked flask, 150 mg (0.45 mmoL) of bergenin and 111 mg (0.54 mmoL) of lipoic acid were dissolved in 40 mL of tetrahydrofuran in a molar ratio of 1:1.2 under nitrogen atmosphere. A catalytic amount of EDC was slowly added under magnetic stirring, the temperature was raised to 60° C., and the reaction was carried out for 12 hours. The reaction was traced to completion by thin layer chromatography, and the heating was stopped. The reaction mixture system was transferred to a separatory funnel, and the lower phase was collected and concentrated to obtain crude bergenin lipoic acid ester. The crude bergenin lipoic acid ester was added to a pear-shaped separatory funnel, and water and chloroform were added. The lower organic layer was collected, dried over anhydrous sodium sulfate, and concentrated under reduced pressure to obtain bergenin lipoic acid ester, 113 mg, a yield of 48.9%.

Example 5

Preparation of Bergenin Lipoic Acid Ester

In a 100 mL three-necked flask, 100 mg (0.31 mmoL) of bergenin and 77 mg (0.37 mmoL) of lipoic acid were dissolved in 40 mL of tetrahydrofuran in a molar ratio of 1:1.2 under nitrogen atmosphere. A catalytic amount of DCC was slowly added under magnetic stirring, the temperature was raised to 60° C., and the reaction was carried out for 12 hours. The reaction was traced to completion by thin layer chromatography, and the heating was stopped. The reaction mixture system was transferred to a separatory funnel, and the lower phase was collected and concentrated to obtain crude bergenin lipoic acid ester. The crude bergenin lipoic acid ester was added to a pear-shaped separatory funnel, and water and chloroform were added. The lower organic layer was collected, dried over anhydrous sodium sulfate, and concentrated under reduced pressure to obtain bergenin lipoic acid ester, 77 mg, a yield of 48.2%.

Example 6

Preparation of Bergenin Lipoic Acid Ester

In a 100 mL three-necked flask, 150 mg (0.45 mmoL) of bergenin and 111 mg (0.54 mmoL) of lipoic acid were dissolved in 40 mL of tetrahydrofuran in a molar ratio of 1:1.2 under nitrogen atmosphere. A catalytic amount of concentrated sulfuric acid was slowly added under magnetic stirring, the temperature was raised to 60° C., and the reaction was carried out for 12 hours. The reaction was traced to completion by thin layer chromatography, and the heating was stopped. The reaction mixture system was transferred to a separatory funnel, and the lower phase was collected and concentrated to obtain crude bergenin lipoic acid ester. The crude bergenin lipoic acid ester was added to a pear-shaped separatory funnel, and water and chloroform were added. The lower organic layer was collected, dried over anhydrous sodium sulfate, and concentrated under reduced pressure to obtain bergenin lipoic acid ester, 108 mg, a yield of 46.7%.

Example 7

The Antioxidant Activity of Bergenin Lipoic Acid Ester Measured by a DPPH Radical Scavenging Activity Assay 2,2-Diphenyl-1-picryl hydrazyl (DPPH) is an organic compound composed of a stable organic radical. In the DPPH molecule, due to the presence of multiple electron-withdrawing —$NO_2$ and large $\pi$ bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical in the sample solution, and the ability of the sample to provide hydrogen atoms and scavenge free radicals can be measured.

Preparation of DPPH solution: measuring exact amount of 2,2-diphenyl-1-picryl hydrazyl (DPPH) and dissolving in methanol to prepare a 0.2 mmol/L DPPH solution, stored at 0° C. in dark.

Preparation of test solutions: Vc (vitamin C, positive control), bergenin lipoic acid ester (sample), bergenin (control), lipoic acid (control), and mixture of bergenin and lipoic acid (reference). The test solutions were serially diluted with acetonitrile, and four groups of controls were separately dissolved in a test tube with a certain amount of methanol to prepare the same concentration gradient as the sample. The corresponding 4 sets of control solutions were obtained (gradient settings are shown in Table 1).

TABLE 1

Dilution gradient of the test solution

| Number | Test solution | Concentration gradient/ppm |
|---|---|---|
| A | Vitamin C | 7.02, 140.4, 702, 2808, 7020, 17550 |
| B | Bergenin lipoic acid ester | 7.02, 140.4, 702, 2808, 7020, 17550 |
| C | Bergenin | 7.02, 140.4, 702, 2808, 7020, 17550 |
| D | Lipoic acid | 7.02, 140.4, 702, 2808, 7020, 17550 |
| E | Bergenin and lipoic acid mixture (1:1) | 7.02, 140.4, 702, 2808, 7020, 17550 |

Specific Steps:

Absorbance measurement: Take 2 mL of sample solution (Table 1, number B), add 2 mL of DPPH solution with concentration of $2*10^{-4}$ moL/L, mix and react in the dark at room temperature for 30 min, adjust to zero with methanol, and measure at 517 nm. The absorbance Ai was simultaneously measured for the absorbance Aj of 2 mL of methanol mixed with 2 mL of the sample solution and the absorbance Ao of 2 mL of DPPH solution mixed with 2 mL of acetonitrile (The experimental results are shown in Table 2).

TABLE 2

Absorbance test results of each test solution

| Sample | Absorbance | Concentration/ppm | | | | | |
|---|---|---|---|---|---|---|---|
| | | 7.02 | 140.4 | 702 | 2808 | 7020 | 17550 |
| B | Ai | 0.993 | 0.621 | 0.461 | 0.257 | 0.230 | 0.223 |
| | Aj | 0.194 | 0.189 | 0.200 | 0.201 | 0.204 | 0.205 |
| | Ao | 1.103 | | | | | |
| C | Ai | 1.176 | 1.128 | 0.996 | 0.723 | 0.313 | 0.249 |
| | Aj | 0.195 | 0.196 | 0.194 | 0.195 | 0.197 | 0.209 |
| | Ao | 1.162 | | | | | |
| D | Ai | 1.023 | 0.994 | 0.826 | 0.622 | 0.373 | 0.292 |
| | Aj | 0.192 | 0.199 | 0.196 | 0.210 | 0.195 | 0.199 |
| | Ao | 1.044 | | | | | |
| E | Ai | 1.074 | 0.925 | 0.560 | 0.244 | 0.244 | 0.233 |
| | Aj | 0.190 | 0.191 | 0.193 | 0.195 | 0.208 | 0.216 |
| | Ao | 1.086 | | | | | |

Clearance calculation: clearance rate (%) [1−(Ai−Aj)/Ao]*100%

TABLE 3

| | DPPH clearance rate experiment results | | | | |
|---|---|---|---|---|---|
| Concentration/ | Clearance rate/% ( n = 3) | | | | |
| ppm | Vc | B | C | D | E |
| 0.00 | 0.00 | 0.00 | 0.00 | 0.00 | 0.00 |
| 7.02 | 82.01 | 27.56 | 15.57 | 20.40 | 18.60 |
| 140.4 | 95.17 | 60.83 | 19.79 | 28.64 | 32.41 |
| 702 | 95.70 | 76.34 | 30.98 | 39.66 | 66.21 |
| 2808 | 99.90 | 94.92 | 54.56 | 60.54 | 90.49 |
| 7020 | 99.90 | 97.64 | 90.01 | 82.95 | 91.67 |

According to the experimental results of FIG. 1, bergenin lipoic acid ester (B) showed a significant scavenging effect on DPPH in a concentration-dependent manner. Its DPPH clearance rate ranges from 27.56% (7.02 ppm) to 97.64% (7020 ppm), with a single bergenin (C), lipoic acid (D), and a mixture of bergenin and lipoic acid (1:1). The scavenging effect of B on DPPH is better than E, and is close to the scavenging ability of Vc when the concentration reaches above 2808 ppm. The above experimental results show that bergenin lipoic acid ester has excellent antioxidant activity and a good application prospect.

What is claimed is:

1. A method of preparing a compound of the following formula (I):

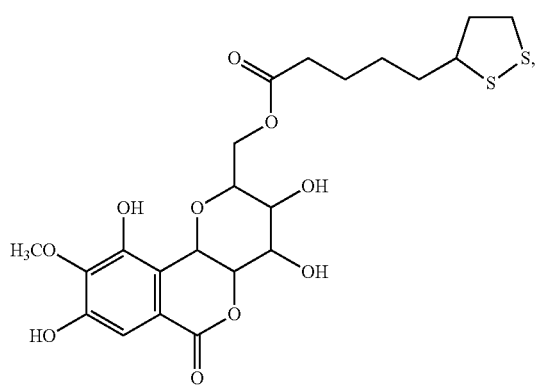

comprising:

reacting a compound of formula (II) with a compound of formula (III) to obtain the compound of formula (I):

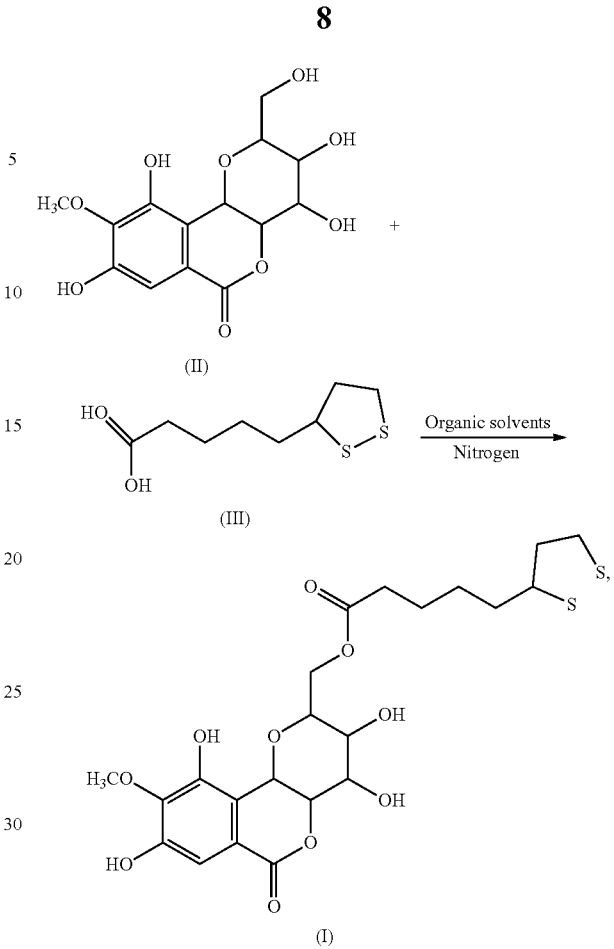

wherein the reaction of the compound of formula (II) with the compound of formula (III) comprises the following steps:

placing the compound of formula (II) and the compound of formula (III), in a molar ratio of 1:1 to 1:1.5, in a reactor;

adding an organic solvent and a catalyst to obtain a reaction mixture under nitrogen atmosphere; and heating the reaction mixture at 50-60° C. for 10-12 hours under sonication, wherein the organic solvent is acetonitrile or tetrahydrofuran, and wherein the catalyst is N,N'-dicyclohexylcarbodiimide, 1-ethyl-3-(3-dimethylaminopropyl)carbodiimide, or sulfuric acid.

2. The method of claim 1, wherein the organic solvent is acetonitrile.

3. The method of claim 1, wherein the molar ratio of the compound of formula (II) and the compound of formula (III) is 1:1.2.

4. The method of claim 1, wherein the catalyst is 1-ethyl-3-(3-dimethylaminopropyl)carbodiimide.

5. The method of claim 1, wherein the reaction mixture is heated at 60° C.

6. The method of claim 1, wherein the reaction mixture is heated for 12 hours.

* * * * *